(12) United States Patent
Msika et al.

(10) Patent No.: US 8,765,198 B2
(45) Date of Patent: Jul. 1, 2014

(54) ANTI-STRETCH MARK ACTIVE AGENT, AND COMPOSITIONS CONTAINING SAME

(75) Inventors: Philippe Msika, Versailles (FR); Caroline Baudouin, Rambouillet (FR); Dalale Naaimi, Epernon (FR); Franck Menu, Sorel Moussel (FR)

(73) Assignee: Laboratoires Expanscience, Courbevoie (FR)

( * ) Notice: Subject to any disclaimer, the term of this patent is extended or adjusted under 35 U.S.C. 154(b) by 133 days.

(21) Appl. No.: 13/128,103

(22) PCT Filed: Nov. 9, 2009

(86) PCT No.: PCT/EP2009/064860
§ 371 (c)(1),
(2), (4) Date: Jul. 14, 2011

(87) PCT Pub. No.: WO2010/052327
PCT Pub. Date: May 14, 2010

(65) Prior Publication Data
US 2011/0268759 A1    Nov. 3, 2011

(30) Foreign Application Priority Data
Jul. 11, 2008  (FR) ..................... 08 57579

(51) Int. Cl.
```
A61K 36/13     (2006.01)
A61K 36/48     (2006.01)
A61K 36/00     (2006.01)
A61K 36/02     (2006.01)
A61K 31/715    (2006.01)
A61K 38/00     (2006.01)
```

(52) U.S. Cl.
USPC ...... 424/770; 424/757; 424/725; 424/195.17; 514/54; 514/18.8

(58) Field of Classification Search
None
See application file for complete search history.

(56) References Cited

U.S. PATENT DOCUMENTS

| | | |
|---|---|---|
| 4,818,751 A | 4/1989 | Ibe |
| 2001/0036933 A1 | 11/2001 | Richards |
| 2007/0128128 A1 | 6/2007 | Thorel et al. |
| 2008/0194476 A1 | 8/2008 | Piccirilli et al. |
| 2009/0010904 A1 | 1/2009 | Iwai et al. |

FOREIGN PATENT DOCUMENTS

| | | |
|---|---|---|
| CA | 2 346 384 | 7/2011 |
| DE | 10 2005 007 482 A1 | 9/2006 |
| EP | 0 668 072 A1 | 8/1995 |
| EP | 0 668 072 B1 | 8/1995 |
| EP | 0 866 808 B1 | 2/2001 |
| EP | 0 939 771 B1 | 5/2003 |
| EP | 1 753 393 A1 | 6/2005 |
| EP | 1 600 461 A1 | 11/2005 |
| FR | 2 836 378 A1 | 8/2003 |
| FR | 2 863 887 | 6/2005 |
| JP | 2006-052197 | 2/2006 |
| KR | 2001/0046576 | 6/2001 |
| WO | WO 97/21734 A1 | 6/1997 |
| WO | WO 98/22512 A1 | 5/1998 |
| WO | WO 99/55736 A2 | 11/1999 |
| WO | WO 00/19974 A1 | 4/2000 |
| WO | WO 2005/063194 A2 | 7/2005 |
| WO | WO 2005/105123 A1 | 11/2005 |
| WO | WO 2006/025068 A1 | 3/2006 |
| WO | WO 2007/099997 A1 | 9/2007 |
| WO | WO 2007/122422 A2 | 11/2007 |
| WO | WO2007122422 A * | 11/2007 |
| WO | WO 2008/080443 A2 | 7/2008 |

OTHER PUBLICATIONS

Adatto et al., "Striae treated by a novel combination treatment—sand abrasion and a patent mixture containing 15% trichloracetic acid followed by 6-24 hours of a patent cream under plastic occlusion," Journal of Cosmetic Dermatology, vol. 2, pp. 61-67, 2004.

French Search Report issued in application No. FR 0857579 on Jun. 19, 2009.

International Search Report issued in application No. PCT/EP2009/064860 issued on Mar. 2, 2010.

Osman et al., "Risk factors for the development of striae gravidarum," American Journal of Obstetrics & Gynecology, 196:62.e1-62.e5, 2007.

* cited by examiner

Primary Examiner — Chris R Tate
Assistant Examiner — Russell Fiebig
(74) Attorney, Agent, or Firm — Foley & Lardner LLP

(57) ABSTRACT

The invention relates to a method for the cosmetic prevention and/or treatment of stretch marks on the skin, characterised in that the method comprises administering a composition containing arabinogalactan as an active principle to a person that may develop or has stretch marks. Said cosmetic composition can be administered in a topical or oral manner.

11 Claims, 11 Drawing Sheets

ANTI-STRETCH MARK ACTIVE AGENT, AND COMPOSITIONS CONTAINING SAME

The present invention relates to a novel anti-stretch mark active agent, arabinogalactan, and to cosmetic and dermatological compositions containing same.

INTRODUCTION

Stretch marks (striae distensae) are cutaneous lines or bands which appear following excessive distension of the skin (weight gain) and hormonal changes. These cutaneous lines or bands are parallel and elongated and are 5 to 15 centimeters in length and 0.2 to 1 centimeter in width. They can be thin and hardly noticeable, but they sometimes form small depressions which give the skin a crumpled appearance. Stretch marks vary at the beginning from pale pink to purplish red (immature or inflammatory stretch marks). They tend to change color over time and become pearl-white (mature stretch marks). They then become less noticeable, but the scar remains. Stretch marks generally concern women during puberty or pregnancy. Approximately 50% to 70% of pregnant women will develop stretch marks, which generally appear between the sixth and eighth month. Very young women more frequently develop stretch marks (20% of adolescents have severe stretch marks) and certain factors promote them such as a first pregnancy, multiple pregnancies and rapid and excessive weight gain (more than 15 kg). Genetic factors and heredity also exert an influence on their appearance. Pregnancy-related stretch marks occur in particular on the anterior surface of the abdomen, but they also occur on the breasts, thighs and hips.

Stretch marks can also appear during physiological or pathological states such as obesity, a relatively intensive diet, tuberculosis and typhoid fever. They can also be a sign of certain rare genetic diseases such as Prader-Willi syndrome, Laurence-Moon-Biedel syndrome and Ehlers-Danlos syndrome. They can also indicate overproduction of cortisol by the suprarenal glands, a disorder called Cushing's syndrome. This syndrome can be caused by a tumor of the pituitary gland or suprarenal glands or by prolonged use of corticoids used in the treatment of certain diseases such as asthma.

Stretch marks arise due to the effect of a too fast and sudden stretching of the skin. Each stretch mark resembles a tear of the skin. It is the dermal tissue which is actually altered, and the target cell of this damage is the fibroblast. The fibroblast undergoes phenotypic change as it is transformed into a myofibroblast by mechanical distensions, and its metabolism is altered by the hormonal environment. Indeed, during pregnancy, the increase in hormones leads to a natural rise in corticoids, which inhibit the activity of fibroblasts by antimitotic action. Thus, the metabolism of these cells is slowed. Moreover, corticoids act on conjunctive tissue metabolism by limiting the synthesis of collagen and elastin, while activating their degradation. During pregnancy, the skin is thus particularly weakened. In addition, this process is accompanied by an inflammatory phase. Consequently, there is degeneration of dermal tissue leading to the formation of an atrophic dermal scar.

The principal triggering factors are thus inflammation, mechanical stress and the hormonal environment. In the end, this set of factors causes stretching, disorientation and disorganization of collagen and elastin fibers, without rupture of the supporting tissue. The major cause of elastic rupture also comes from a lack of water in the cells. From the first signs of dehydration collagen fibers form numerous and more frequent branches, due to tension, lose their elasticity and visibly break on the dermis.

Thus, in a recent stretch mark, which appears as a purplish-red streak, there is inflammation which disorganizes and destroys the fibers of the skin. Gradually, inflammation and redness decrease and fibroblasts attempt to synthesize new fibers to fill the void. However, these new fibers are of lower quality than the old. After a few months, the old stretch mark becomes pearl-white and shiny.

Stretch marks are comparable to scars (because they undergo the same stages of formation as following trauma to the skin); their complete healing is currently impossible, but it is possible to attenuate and improve the lesions. Curative treatments are essentially local: use of topical compounds with tretinoin (all-trans retinoic acid) or fruit acids, use of peeling or laser. Tretinoin has anti-stretch mark action that tends to essentially restore the network of fibrillins.

Considering the physiopathology of stretch marks, the prevention and reduction of nascent stretch marks related to pregnancy require the use of a product that targets dermal fibroblasts and that can act by activating cell proliferation and by stimulating metabolism, in particular the neosynthesis of the principal macromolecules responsible for skin elasticity and tonicity (collagens and elastin). In addition, it is also necessary to limit the inflammation that participates in the degradation of macromolecules of the dermal matrix.

PRIOR ART

Application WO 00/19974 describes a cosmetic method for preventing the appearance of stretch marks and/or for treating stretch marks. The proposed cosmetic composition contains at least one anti-stretch mark agent selected from soya peptides, tripeptides composed of the amino acids glycine, histidine and lysine, and mixtures of said peptides.

If this composition of the prior art makes it possible to obtain a stretch mark regression effect, it is not completely suited to the particular case of stretch marks that appear during pregnancy, and notably to prevent their appearance.

There is a real demand for the development of a product for effectively preventing and/or treating, with acceptable cutaneous tolerance, this complex and particularly unaesthetic phenomenon of stretch marks that appear during pregnancy.

Arabinogalactans (also called galactoarabinans) are polysaccharides. They are present in variable quantities in a number of plants, mushrooms and bacteria. Arabinogalactans are natural soluble fibers which can be extracted from bacteria or from plants such as coffee or larches.

Arabinogalactan is a polymer composed of two types of saccharides, galactose and arabinose, in a ratio of 6:1, respectively.

Methods for extracting arabinogalactan have been described, in particular from coffee (EP 1 600 461, WO 2007/099997) and from larch (EP 0 866 808). The most common commercially-available arabinogalactans are those from larch, a tree that is particularly arabinogalactan-rich.

To date, the known roles of arabinogalactans on mammalian metabolism are as follows:
1) Arabinogalactans are indigestible fibers which promote the proliferation, in the digestive tract, of bacteria of use to the body. This is referred to as "prebiotic" action.
2) The ingestion of arabinogalactan has the reputation of stimulating the immune system. Application EP 1 600 461 claims in particular the adding of arabinogalactan from coffee beans in food in order to obtain "health foods."

There are all kinds of arabinogalactan derivatives. These derivatives have cosmetic and dermatological applications as described in the following documents:

Patent EP 0 939 771 describes compositions containing lipid arabinogalactan derivatives. Application EP 1 076 547 describes a composition containing an arabinogalactan derivative, and the use of same in cosmetics.

Proteins coupled to arabinogalactans (AGP) have been widely studied, and their role in cosmetics has been described notably in patent EP 0 668 072.

The use of pure arabinogalactan in cosmetics was proposed in application FR 2 836 378, for its protective and stimulatory action on interleukin-12. This use is intended to promote DNA repair.

In a completely surprising way, the inventors of the present application have demonstrated a beneficial effect of arabinogalactan on the treatment and prevention of stretch marks.

DETAILED DESCRIPTION OF THE INVENTION

The present invention relates to a method of cosmetic prevention and/or treatment of stretch marks on the skin, characterized in that the method comprises administering a composition containing arabinogalactan as an active principle to a person that may develop or has stretch marks. Said composition advantageously can be administered in a topical or oral manner.

Due to its nonirritating and moisturizing properties, arabinogalactan makes it possible to significantly reduce insensible water loss. In addition, this polysaccharide has intrinsic exfoliation capacity. These combined actions promote cell renewal.

According to the present invention, the expression "prevention of stretch marks on the skin" refers to an action that makes it possible to avoid or at the very least to reduce the formation of stretch marks, that is to say, their length, width and/or depth, in the context of a cosmetic or dermatological treatment, by application of the composition, before and during an event known to be able to cause the appearance of stretch marks, such as pregnancy.

According to the present invention, the expression "treatment of stretch marks on the skin" refers to an action that makes it possible to cause to regress; that is to say, to reabsorb, in the context of a cosmetic or dermatological treatment, in a visible and measurable way, stretch marks that are already formed, that is to say, their length, width and/or depth.

Thus, the composition used according to the invention can be applied topically to regions of the skin likely to form stretch marks, regions that contain stretch marks in the course of formation or even regions that contain stretch marks that are already formed. These regions are well known to the person skilled in the art and correspond to the regions of the belly, hips, buttocks, thighs and breasts.

The composition can also be administered orally, notably in the form of tablets, hard capsules, soft capsules, sugar-coated pills, emulsions, gels, or in the form of dietary supplements or foods.

According to a preferred embodiment of the invention, the arabinogalactan used is extracted from larch. An extraction process is described in particular in patent application EP 0 866 808.

Preferentially, the anti-stretch mark composition according to the invention contains arabinogalactan in a proportion between 0.01% and 10% by weight, advantageously between 1% and 5% by weight, and more preferentially in a proportion of approximately 2% by weight compared to the total weight of the composition.

According to a preferred embodiment of the invention, the anti-stretch mark composition contains at least one other anti-stretch mark agent, and in particular:

lupeol,
soya peptides,
tripeptides composed of the amino acids glycine, histidine and lysine,
sophora, (*Sophora japonica*) flower extract,
chlorophyceae (*Enteromorpha compressa*) extract,
peptide extract of avocado,
panthenol,
as well as the various mixtures of said compounds.

Each of the aforesaid compounds has its own action aimed at amplifying or promoting the action of arabinogalactan on stretch marks.

Lupeol is a triterpene alcohol present in many plants. The preferred lupeol composition is composed of 5% lupin (*Lupinus albus*) extract and 95% *Helianthus annuus*, seed oil. A lupin seed hull extract containing lupeol can be prepared as described in application WO 02/085827. Lupeol promotes the production of "good collagen" by cells, and acts on fibroblasts by "relaxing" them; the skin is better prepared to face mechanical stresses.

According to the present invention, "soya peptides" can be any peptide obtained by hydrolysis of proteins extracted from soya, according to procedures known to the person skilled in the art; in other words, any soya protein hydrolysate. Soya peptides have elasticity regulation action, which makes it possible to promote skin elasticity.

A soya peptide that is particularly preferred for the composition used according to the invention is a fermented peptide called "Phytokine®" marketed by Coletica.

The expression "tripeptides composed of the amino acids glycine, histidine and lysine" refers to in particular tripeptides of the sequence Gly-His-Lys, whose amino acids can be in D, L or DL form, optionally conjugated with a carboxylic acid such as acetic acid, in the form of a complex with a metal such as zinc or copper.

*Sophora japonica*, flower extract is rich in flavonoids and rutin. This extract can notably refer to a composition containing 22.5% flower extract, 55% butylene glycol and 22.5% water. It is a compound that contributes secondarily to the anti-stretch mark action, which takes part in controlling the vascularization of stretch marks and thus their color.

The expression "chlorophyceae extract" notably refers to an extract of *Enteromorpha compressa*. Advantageously, a composition containing 20% *Enteromorpha compressa*, contained in a mixture of butylene glycol (40%) and glycerin (40%) will be used. This compound has a soothing action that reduces desquamation, the feeling of skin tightness and erythema. It improves the comfort of delicate, sensitive and dry skin.

The expression "peptide extract of avocado" notably refers to an extract as described in international application WO 2005/105123, wherein said extract is characterized in that it contains 2% to 10% by weight alpha-amino nitrogen compared to the weight of the dry matter of the peptide extract. This peptide extract can be obtained directly from any part of the avocado or avocado tree, such as the fruit, flesh, pit, leaves or roots of the avocado tree. The fruits may be selected from the following varieties: Hass, Fuerte, Ettinger, Bacon, Nabal, Anaheim, Lula, Reed, Zutano, Queen, Criola Selva, Mexicana Canta, Region Dschang, Hall, Booth, Peterson or Collinson Red. More advantageously, the fruits are selected from the Hass, Fuerte and Reed varieties.

Dextrorotatory panthenol is a provitamin arising from D-pantothenic acid. It stimulates the formation of cells, moisturizes and soothes.

Others compounds can advantageously be added to the composition according to the invention, such as sodium lactate methylsilanol or dietary minerals containing copper and zinc, such as zinc gluconate and copper gluconate.

The dermatological composition according to the invention can further contain at least one compound selected from the group comprising anti-irritant and/or soothing and/or healing and/or anti-aging and/or moisturizing agents.

The anti-irritant and/or soothing and/or healing and/or anti-aging and/or moisturizing agents that can be used in the context of the present invention in combination with arabinogalactan are advantageously glycine, sugars and/or peptides of plants including lupin, lupeol (FR 2 822 821, FR 2 857 596), oxazolines (WO 04/112741, WO 2006/114443), oxazolidinones (WO 04/05005), lipoic acid, alpha bisabolol, licorice derivatives, enoxolone, ectoine, Avocadofurane® (avocado furans, capable of being obtained by the process described in international application WO 01/21605), *Centella asiatica*, extracts, in particular madecassic acid or Asian acid, caffeine, retinol, retinal, retinoic acid, zinc oxide, magnesium, silicon, copper, zinc, manganese, selenium, hyaluronic acid, azelaic acid and the salts or esters thereof, salicylic acid and derivatives thereof, alpha hydroxy acid (AHA), AHA esters, pyrrolidone carboxylic acid and derivatives thereof, ceramides, cholesterol, squalane, phospholipids, beta carotene, vitamin A, vitamin E, vitamin C, vitamin B3, (niacinamide, nicotinamide), vitamin B5, (panthenol), vitamin B6, benzoyl peroxide, urea, coenzyme Q10, glucosamine and salts thereof, N-acetyl glucosamine, spring waters or thermal waters (Avène, Roche Posay, Saint Gervais, Uriage, Gamarde) and soya peptides.

The oxazolines that can be used in the context of the present invention in combination with arabinogalactan are advantageously oxazolines selected from the group comprising 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. In an even more advantageous way, the aforesaid oxazoline is 2-undecyl-4,4-dimethyl-1,3-oxazoline, called OX-100, or Cycloceramide®.

In addition to these active agents, the arabinogalactan according to the invention, alone or in combination with the active agents cited above, can be used in combination with avocado sugars, agents that restructure the cutaneous barrier, antifungal compounds, antiseptic preservatives and compounds containing vegetable oil unsaponifiables, lupin peptides, avocado oil, butyl avocadate, cycloceramides, genistein, colza concentrates and corn concentrates.

The avocado sugars are advantageously D-mannoheptulose and/or perseitol. The avocado sugars correspond more advantageously to the water-soluble extract of avocado sugars described in application WO 2005/115421.

The agents that restructure the cutaneous barrier, making it possible to stimulate the synthesis of the key lipids of the epidermis, and that can be used in the context of the present invention in combination with arabinogalactan are advantageously concentrates of sunflower, even more advantageously linoleic concentrates of sunflower, such as the active agent marketed by Expanscience Laboratories, Soline® (see international application WO 01/21150), vegetable oil unsaponifiables, such as Avocadofurane® (see international application WO 01/21150) and PPAR agonists (rosiglitazone, pioglitazone).

The antifungal compounds that can be used in the context of the present invention in combination with arabinogalactan are advantageously econazole and ketoconazole.

The antiseptic preservatives that can be used in the context of the present invention in combination with arabinogalactan are for example triclosan, chlorhexidine or quaternary ammoniums.

The compounds containing vegetable oil unsaponifiables that can be used in the context of the present invention in combination with arabinogalactan are advantageously selected from the group comprising avocado furanic lipids, avocado unsaponifiables, soya unsaponifiables, avocado and soya unsaponifiables, lupin oil concentrates, sunflower oil concentrates and mixtures thereof.

The avocado furanic lipids that can be used in the context of the present invention in combination with arabinogalactan are advantageously natural 2-alkyl furans, notably the active agent Avocadofurane® marketed by Expanscience Laboratories, which can be obtained by the process described in international application WO 01/21605.

The avocado and soya unsaponifiables that can be used in the context of the present invention in combination with arabinogalactan are advantageously a mixture of furanic unsaponifiables of avocado and unsaponifiables of soya, in a ratio of about 1:3-2:3, respectively. The avocado and soya unsaponifiables are even more advantageously the product Piascledine®, marketed by Expanscience Laboratories.

The lupin oil concentrates that can be used in the context of the present invention in combination with arabinogalactan are advantageously concentrates obtained by molecular distillation of lupin oil, advantageously sweet white lupin oil, such as those described in international application WO 98/47479. They advantageously contain approximately 60% unsaponifiables by weight.

The sunflower oil concentrates that can be used in the context of the present invention in combination with arabinogalactan are advantageously linoleic sunflower concentrates, such as the active agent marketed by Expanscience Laboratories, Soline® (see international application WO 01/21150).

According to a preferred embodiment of the invention, the composition contains both arabinogalactan and lupeol. According to another preferred embodiment, the composition contains arabinogalactan, lupeol and soya peptides. Lastly, the preferred composition contains arabinogalactan, lupeol, soya peptides and a peptide extract of avocado. The combination of these four components confers on the composition a remarkable anti-stretch mark action, with these four compounds acting in synergy to protect the skin. Such a composition makes it possible to obtain a particularly beneficial effect on existing stretch marks, as well as on the prevention of their appearance.

The topical composition according to the invention also contains a suitable carrier which can be any carrier among those known to the person skilled in the art in order to obtain a cosmetic or dermatological composition that can be used according to the invention, in particular in the form of a cream, lotion, gel, spray, patch, water, pomade, milk or oil, optionally in emulsion form, with additional components known to the person skilled in the art to improve, modify or stabilize the composition from a cosmetic or dermatological point of view.

For oral ingestion, numerous forms are possible, in particular dietary supplements. They are formulated by the usual processes to produce tablets, hard capsules, soft capsules, sugar-coated pills, emulsions and gels. In particular, arabinogalactan and the other active agents of the invention can be incorporated in all forms of dietary supplements or enriched foods, for example, food bars, compacted or non-compacted powders, beverages, dairy products and in particular yogurts and drinkable yogurts. The powders can be diluted in water, sodas, fruit juices, dairy products or products containing soya or rice, or can be incorporated in food bars.

The procedures for preparing these compositions according to the invention are part of the general knowledge of the person skilled in the art.

The aforesaid composition according to the invention is particularly intended to prevent the appearance of stretch marks during pregnancy, or generally when the hormonal environment is unfavorable for fibroblast metabolism.

Lastly, the present invention relates to the cosmetic use of arabinogalactan, or a composition such as defined above, to prevent and/or treat the appearance of stretch marks on the skin, in particular during pregnancy.

Another object of the invention is the use of arabinogalactan, or a composition such as defined above, to obtain a dermatological composition intended to prevent and/or treat the appearance of stretch marks on the skin.

The following examples are intended to illustrate the present invention and should in no case be interpreted as restricting the scope of the invention.

EXAMPLES

Figure 1:
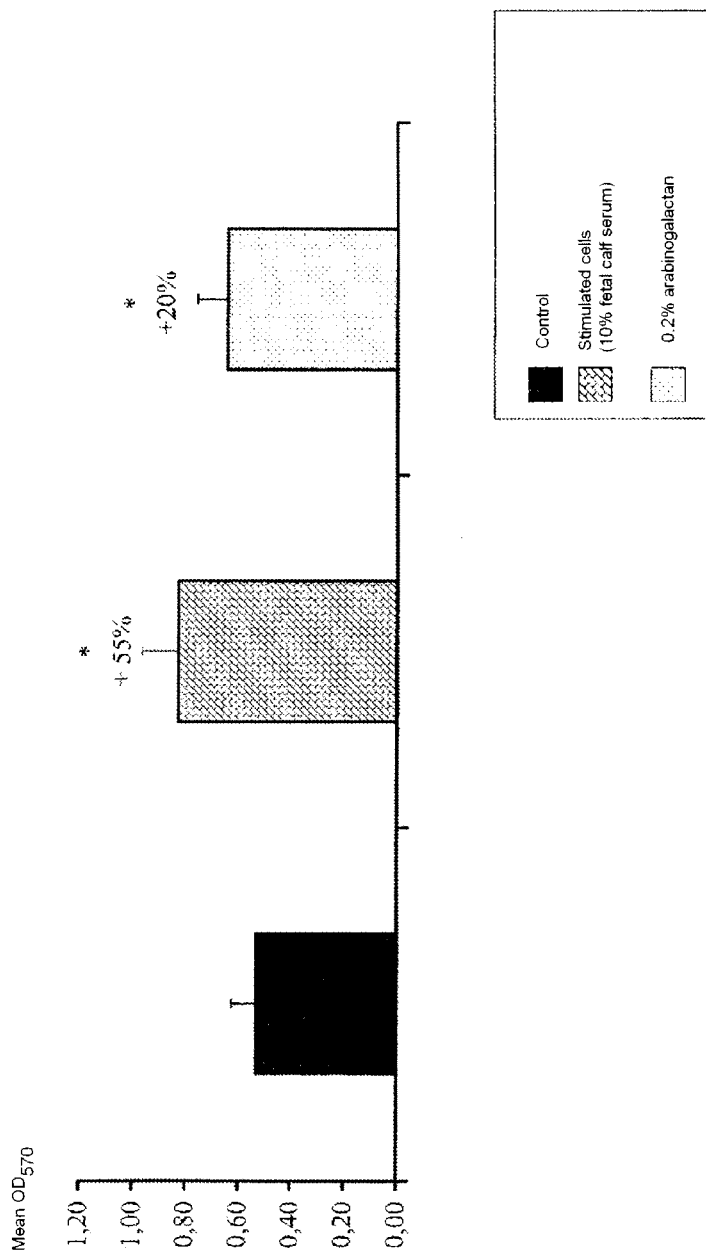
FIG. 1: Study of the proliferation of fibroblasts in the presence of arabinogalactan (mean $OD_{570}$)

The effects of arabinogalactan, used at a concentration of 0.2% dry matter, were analyzed on the following parameters:
Fibroblast proliferation;
Expression of dermal macromolecules, collagen I and collagen III, under normal conditions and in a deleterious hormonal environment mimicking that of pregnancy;
Inflammation.

A. Prerequisite Cutaneous Tolerance
Inflammation:
The pro-inflammatory potential of arabinogalactan was evaluated on normal human keratinocytes. Interleukins 1 and 8 as well as TNF-α, early mediators of inflammation, were assayed in the cell supernatant.

At a concentration of 0.2% dry matter (DM), arabinogalactan does not lead to salting out of interleukins 1 and 8 or TNF-α. Arabinogalactan is thus not pro-inflammatory.

B. Biological Activity Study Methods
1. Study of Fibroblast Proliferation by the MTT Method
The MTT [3-(4,5-dimethylthiazol-2-yl)-2,5-diphenyltetrazolium bromide] assay is a colorimetric test which measures cell viability. MTT is a yellow water-soluble tetrazolium salt; metabolically active cells are capable of reducing it into formazan blue crystals.

At D0, the fibroblasts are inoculated in RPMI medium with 1% FCS.

At D1, the cells are treated with RPMI with 10% FCS (positive control) or with 0.2% arabinogalactan for 48 hours.

At the end of the treatment, cell viability is quantified by an MTT assay: after 3 hours of contact with MTT, the formazan crystals formed are solubilized by DMSO and the optical density, proportional to the quantity of metabolically active and thus living cells, is read at 570 nm against the blank (without cells).

2. Study of the Expression of Genes Coding for Collagens I and III by RT-PCR
Principle of Quantitative Real-Time PCR:
The quantitative real-time polymerase chain reaction (qRT-PCR) is a method that makes it possible to measure in a specific and quantitative way the expression of genes of interest by amplification. Quantification is based on the real-time monitoring of gene amplification using SYBR Green as a reporter system. SYBR Green is a molecule with fluorescent properties which is intercalated in double-stranded DNA. The PCR is run in a succession of temperature cycles in three stages:

Denaturation: separation of the two DNA strands.
Hybridization: recognition of a DNA sequence corresponding to a target gene by virtue of specific primers.
Extension: of the sequence of interest by action of a polymerase.

At the end of the reaction, quantification is carried out by analyzing the "cycle threshold" (Ct: the point at which the fluorescence emission signal is statistically and significantly higher than the background noise). The quantities of DNA are compared in the exponential part, the time during which the increase in the quantity of DNA is proportional to the initial quantity of the matrix.

Protocols
Effect of Arabinogalactan on the Gene Expression of Collagens I and III in Normal Fibroblasts
Fibroblasts were inoculated in RPMI medium with 1% FCS.

Twenty-four hours later, the cells were treated with 5 ng/ml TGF-β1 or 0.2% arabinogalactan for 48 hours.

Preventive Effect of Arabinogalactan on the Gene Expression of Collagen I in Fibroblasts Treated with Hydrocortisone (Hormonal Environment)
Fibroblasts were pretreated with 0.2% arabinogalactan. After 24 hours of incubation at 37° C., the treatment with arabinogalactan was renewed in the presence of 50 μM hydrocortisone for 48 hours.

The controls used to validate the test were 50 μM hydrocortisone and 5 ng/ml TGF-β.

At the end of the treatment of the cells, total RNA was extracted (RNeasy MiniKit) and then assayed quantitatively in chips using the Experion system (Experion RNA StdSens kit).

Total RNA was then reverse-transcribed in cDNA (iScript cDNA Synthesis kit).

Lastly, the neo-synthesized cDNA relating to the gene of interest or to the reference genes (HPRT, GAPDH, YWHAZ and beta-actin as standards) were selectively amplified by real-time PCR (iQ5, Biorad) using specific primers for the target sequences.

Expression of the genes of reference is analyzed in the same samples as those for which the expression of the genes of interest is evaluated in order to normalize the results.

Analysis of Results

The results are normalized compared to the most stable reference gene (according to the geNorm algorithm):

$$\Delta Ct = Ct_{gene\ of\ interest} - Ct_{most\ stable\ reference\ gene}$$

Variation in the number of copies of the gene of interest during the treatment is then calculated according to the following formula:

$$\Delta\Delta Ct = \Delta Ct_{control} - \Delta Ct_{treatment}$$

Finally, the relative quantity or level of expression of the genes of interest normalized by the level of expression of the reference genes in the untreated and treated samples is obtained by the formula $RQ = 2^{\Delta\Delta Ct}$.

3. Study of Anti-Inflammatory Potential

Keratinocytes were inoculated in KGM2 medium. After 24 hours of incubation, the cells were pre-treated with 0.2% (dry matter) arabinogalactan for 24 hours. Next, the cells were stimulated by adding 10 µg/ml PMA (phorbol-12-myristate-13-acetate; Sigma) for 16 hours, in order to mimic inflammation.

At the end of the treatment, the cell supernatants were collected and IL-1β was assayed using ELISA kits (R&D Systems).

On the cell layers, a neutral red assay was carried out: optical density, proportional to the quantity of living cells, is read at 540 nm.

The quantity of IL-1β is expressed by living cells according to the formula: OD ELISA IL-1β/OD$_{540}$.

4. Statistics

The significance of the results was evaluated by a Student's t-test: *p<0.05, **p<0.01.

C. Results

Example 1

Effect of Arabinogalactan on Fibroblast Proliferation

The prevention and slowing of the appearance of stretch marks require the use of an active agent that promotes cell renewal. Moreover, the activation of cell proliferation stimulates dermal metabolism and promotes the neosynthesis of essential macromolecules of the extracellular matrix such as collagens and elastin.

The effect of arabinogalactan on fibroblast proliferation was evaluated by an MTT test (FIG. 1). The results obtained show that arabinogalactan significantly activates cell regeneration after 48 hours of treatment (+20%).

Arabinogalactan, by thus promoting fibroblast proliferation, enables these reparative cells of the dermis to restart cell metabolism and synthesis of collagen and elastin in the damaged regions.

Example 2

Effect of Arabinogalactan on the Dermal Matrix

A stretch mark results from damage to fibroblastic cells, with a blocking of macromolecule synthesis and a reduction in the level of messenger RNA coding for collagens I and III and for fibronectin. These alterations are a consequence of the hormonal stress (corticoids) that accompanies pregnancy. As a result, a general atrophy of the extracellular matrix (ECM) appears with a decline in the number of fibroblasts and a reduction in collagens I and III.

The effect of arabinogalactan was evaluated on the expression of two macromolecules of the dermal matrix, collagens I and III, under normal conditions and under conditions mimicking the hormonal environment that predisposes the appearance of stretch marks during pregnancy.

a. Effect of Arabinogalactan on Expression of Collagen Type I

Figure 2:
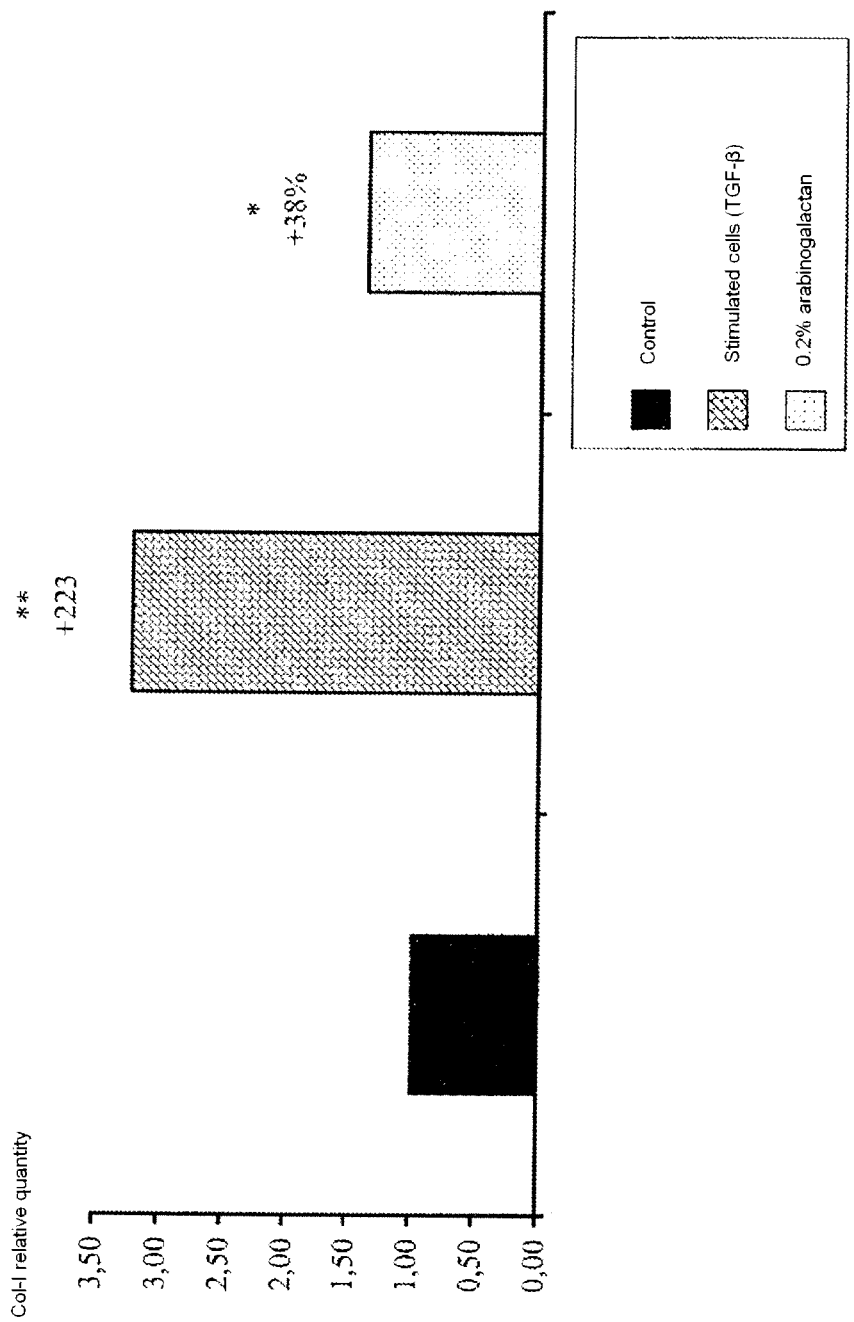
FIG. 2: Gene expression of collagen I in the presence of arabinogalactan (Col-I relative quantity)

The effect of arabinogalactan on the expression of the gene coding for collagen type I was evaluated by real-time PCR after a 48-hour treatment. The relative quantity of collagen measured is normalized compared to the expression of GAPDH. The results presented in FIG. 2 show a significant increase (+38%; p<0.05) of the gene coding for collagen type I in the presence of arabinogalactan.

TGF-β is a growth factor with a strong capacity to induce molecules of the extracellular matrix such as collagens type I and III. It should also be noted that, under the test conditions, TGF-β (used as a positive control) induced a very strong overexpression of the collagen I gene (+223%).

b. Effect of Arabinogalactan on Expression of Collagen Type III

Similarly, after 48 hours of treatment, TGF-β1 very significantly stimulates the expression of the collagen type III gene in fibroblasts (147% increase).

Figure 3:
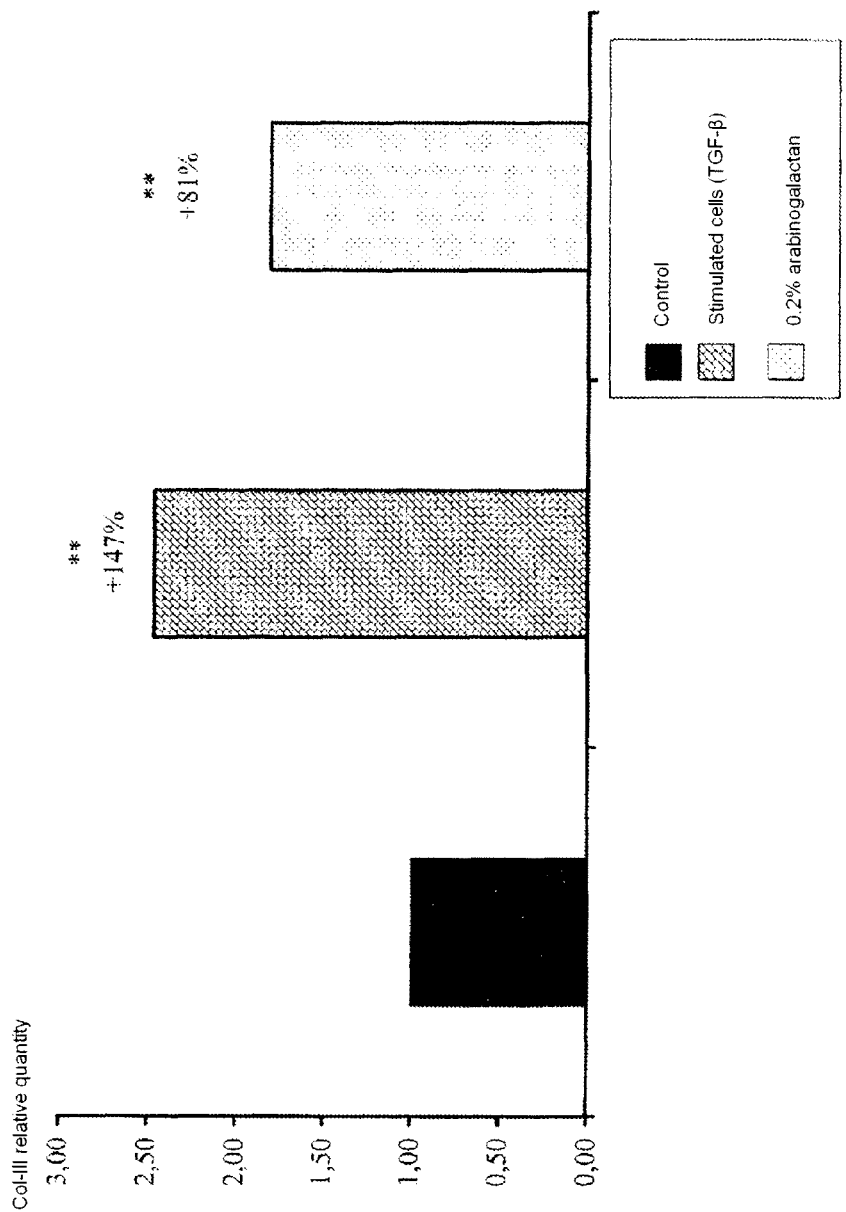
FIG. 3: Gene expression of collagen III in the presence of arabinogalactan (Col-III relative quantity)

Arabinogalactan (0.2% dry matter) very significantly stimulates (+81%) the expression of the collagen type III gene in fibroblasts (FIG. 3).

c. Effect of Arabinogalactan on the Expression of Collagen Type I in Conditions Mimicking the Hormonal Environment Predisposing the Appearance of Stretch Marks During Pregnancy The potential preventive effect of arabinogalactan on the expression of the collagen type I gene was evaluated under conditions mimicking the hormonal environment predisposing stretch marks during pregnancy.

Figure 4:
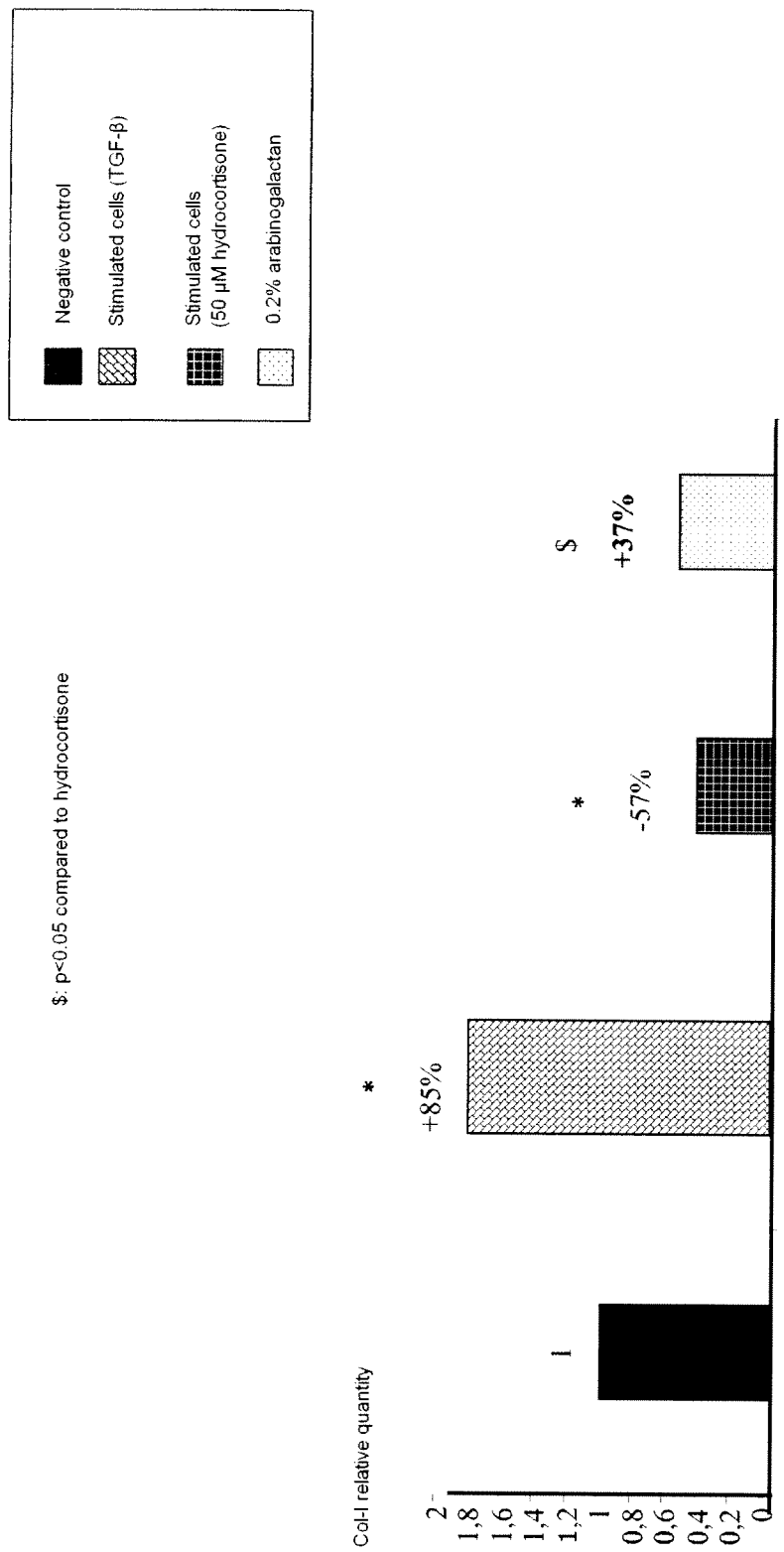
FIG. 4: Preventive effect of arabinogalactan on collagen I gene expression in fibroblasts treated with hydrocortisone (Col-I relative quantity)

In FIG. 4, it is confirmed that the expression of the collagen I gene decreases in the presence of hydrocortisone (57% inhibition after 48 hours of treatment). On the other hand, pretreatment of cells for 24 hours with arabinogalactan counters the inhibiting effect of hydrocortisone and increases the expression of collagen I by 37%.

Arabinogalactan stimulates the expression of collagens type I and III under normal conditions and under conditions that promote the appearance of stretch marks (deleterious hormonal environment). Arabinogalactan thus has a beneficial effect on the components of the dermal extracellular matrix which can be altered during pregnancy, leading to the appearance of stretch marks. Thus, arabinogalactan can slow the appearance of stretch marks.

Example 3

Anti-Inflammatory Effect

The formation of stretch marks is accompanied by an inflammatory phase leading to increased production of inflammatory proteases and cytokines (including interleukin-1, or IL-1). These inflammatory enzymes and cytokines significantly degrade high-quality collagen and elastin fibers and thus alter the dermal matrix.

The potentially anti-inflammatory effect of arabinogalactan on the salting-out of IL-1β was studied.

Figure 5:
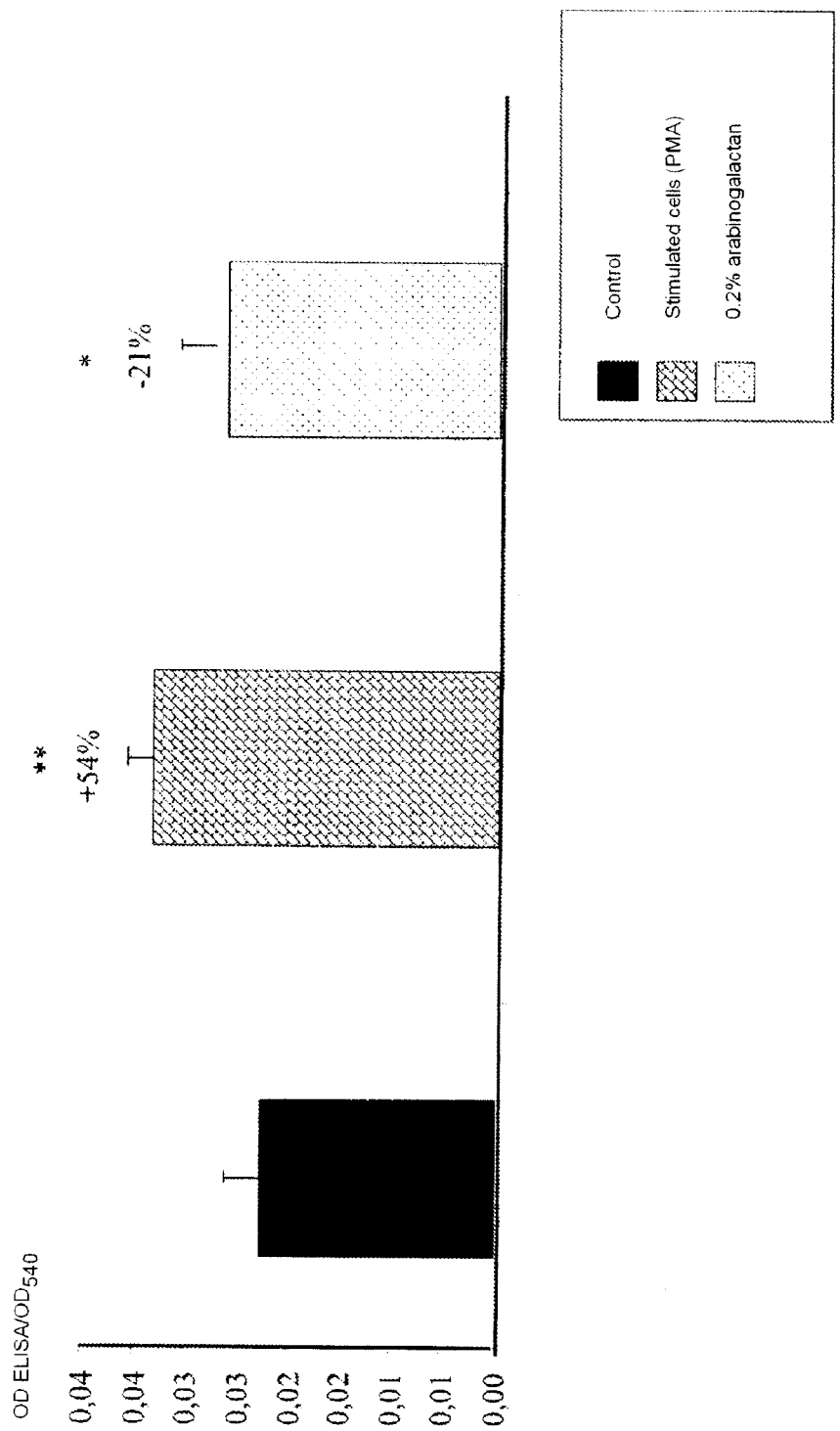
FIG. 5: Anti-inflammatory effect of arabinogalactan with respect to PMA: IL-1β assay (OD ELISA/$OD_{540}$)

As shown in FIG. 5, under the effect of stress by PMA, a pro-inflammatory chemical agent, keratinocytes massively salt-out IL-1β, an early marker of inflammation.

Pretreatment of cells for 24 hours with arabinogalactan significantly inhibits the salting out of IL-1β (−21%).

Arabinogalactan exerts an anti-inflammatory action on the release of inflammatory cytokines. It thus contributes to slow the degradation of the supporting framework of the skin. This anti-inflammatory action contributes to limit the progression of stretch marks.

Example 4

Compositions for Topical Application

The inventors present below several compositions for topical application, particularly indicated for the prevention of stretch marks during pregnancy.

Composition No. 1:
    ARABINOGALACTAN: 0.1% to 10%
    Lupeol: 0.1% to 1%
    Soya peptides: 0.1% to 4%
    22.5% *sophora*, flower extract: 1% to 10%
    Peptide extract of avocado: 0.1% to 1%
    Zinc gluconate: 0.1% to 1%
    Shea (*Butyrospermum parkii*) butter: 1% to 5%
    Candelilla wax: 0.1% to 5%
    Dimalate alcohol: 0.1% to 15%
    Ethylhexyl cocoate: 1% to 5%
    Cetearyl glucoside: 1% to 5%
    Dicaprylyl carbonate: 1% to 10%
    Hydrogenated coco-glycerides: 1% to 5%
    Glyceryl caprylate: 0.1% to 1%
    30% soda solution: 0.1% to 5%
    Lauroyl lysine: 0.1% to 1%
    Capryloyl glycine: 0.1% to 1%
    70% glyceryl stearate & 10% cetearyl alcohol & 10% coco-glycerides & 10% cetyl palmitate: 0.1% to 5%
    Potassium cetyl phosphate: 0.1% to 2%
    Carbomer: 0.1% to 2%
    Fragrance: 0.1% to 1%
    Xanthan gum: 0.1% to 1%
    Purified water: QSP 100%

Composition No. 2:
    ARABINOGALACTAN: 0.1% to 10%
    Lupeol: 0.1% to 1%
    PHYTOKINE® hydrolyzed soya peptides: 0.1% to 5%
    Dimalate alcohol: 0.1% to 15%
    *Sophora*, flower extract: 1% to 10%
    Peptide extract of avocado: 0.1% to 1%
    Octyl cocoate: 1% to 10%
    EMULIUM DELTA: 1% to 10%
    Dextrorotatory panthenol: 1% to 5%
    Zinc gluconate: 0.1% to 1%
    Copper gluconate: 0.1% to 1%
    Shea butter (liquid): 0.1% to 5%
    White beeswax: 0.1% to 5%
    Pure cetyl alcohol: 0.1% to 5%
    Dermosoft GMCY (glyceryl caprylate): 0.1% to 2%
    30% soda: 0.1% to 5%
    Capryloyl glycine: 0.1% to 1%
    Carbopol ultrez 10: 0.1% to 2%
    Fragrance: 0.1% to 1%
    Xanthan gum: 0.1% to 1%
    Purified water: QSP 100%

Arabinogalactan can also be incorporated in various cosmetic products such as cleansing water, oil-in-water emulsions, oils, milks, foams and sprays, the compositions of which are presented below.

| CLEANSING WATER 1 | |
|---|---|
| Brand name | % |
| PURIFIED WATER B4 | QSP 100% |
| BIOSACCHARIDE GUM | 1% to 5% |
| BUTYLENE GLYCOL | 1% to 5% |
| PURIFIED SAPONIN | 0% to 1% |
| ROSE WATER | 0% to 1% |
| ARABINOGALACTAN | 0% to 5% |
| PRESERVATIVES | 0% to 1% |
| ALLANTOIN | 0% to 1% |
| CITRIC ACID MONOHYDRATE | 0% to 1% |
| TROMETHAMINE | 0% to 1% |

| CLEANSING WATER 2 | |
|---|---|
| Raw material/brand name | % |
| CAPRYLOYL GLYCINE | 0% to 1% |
| SODA LYE | 0% to 1% |
| PURIFIED WATER B4 | 20% to 100% |
| SEQUESTRANT | 0% to 1% |
| BUTYLENE GLYCOL | 1% to 5% |
| ARABINOGALACTAN | 0% to 5% |
| OCTANEDIOL | 0% to 1% |
| PEG-32 | 1% to 5% |
| PEG-7 PALMCOCOATE | 1% to 5% |
| ZINC GLUCONATE | 0% to 1% |
| CITRIC ACID MONOHYDRATE | 0% to 1% |
| PURIFIED WATER B4 | QSP 100% |
| FRAGRANCE | 0% to 1% |
| POLOXAMER 184 | 1% to 5% |
| D.S.B. C SP | 1% to 5% |

| Water-in-oil EMULSION | |
|---|---|
| Raw material/brand name | % |
| LIQUID ISOPARAFFIN | 5% to 20% |
| ISOCETYL STEARATE | 5% to 20% |
| HYDROXYSTEARATE AL-MG | 5% to 20% |
| ABIL WE 09 | 1% to 5% |
| GLYCEROL | 1% to 5% |
| THICK VASELINE OIL | 1% to 5% |
| MICRONIZED ZINC OXIDE | 1% to 5% |
| BUTYLENE GLYCOL | 1% to 5% |
| ARABINOGALACTAN | 0% to 5% |
| ISONONYL ISONONANOAT | 1% to 5% |
| WHITE BEESWAX | 1% to 5% |
| SODIUM TARTRATE | 1% to 5% |
| SODIUM CHLORIDE | 0% to 5% |
| GLYCINE | 1% to 5% |
| OCTANEDIOL | 0% to 1% |
| CHOLESTEROL | 0% to 1% |
| PHYTOSPHINGOSINE | 0% to 1% |
| TARTARIC ACID | 0% to 1% |
| PURIFIED WATER B4 | QSP 100% |

| Oil-in-water EMULSION | |
|---|---|
| Raw material/brand name | % |
| HYDROGENATED POLYDECENE | 5% to 20% |
| LAURYL GLUCOSIDE- | 1% to 5% |

| Oil-in-water EMULSION | |
|---|---|
| Raw material/brand name | % |
| GLYSTEARATE | |
| DICAPRYLYL CARBONATE | 1% to 5% |
| GLYCEROL | 5% to 20% |
| CARBOPOL ETD 2020 | 0% to 1% |
| XANTHAN GUM | 0% to 1% |
| ARABINOGALACTAN | 0% to 5% |
| SODA LYE | 0% to 1% |
| PRESERVATIVES | 0% to 1% |
| CITRIC ACID MONOHYDRATE | 0% to 1% |
| PURIFIED WATER B4 | QSP 100% |

| OIL | |
|---|---|
| Raw material/brand name | % |
| SOLUBILIZER | 0% to 1% |
| SWEET ALMOND OIL | 5% to 20% |
| CAPRYLATE/COPRA CAPRATE | QSP 100% |
| REFINED MACADAMIA OIL | 5% to 20% |
| GLYCEROL CAPRYLOCAPRATE | 5% to 20% |
| ALPHA BISABOLOL NAT | 0% to 1% |
| ALPHA TOCOPHEROL | 0% to 1% |
| ARABINOGALACTAN | 0% to 5% |
| PRESERVATIVE | 0% to 1% |
| ESTER | 0% to 1% |

| MILK | |
|---|---|
| Raw material/brand name | % |
| SWEET ALMOND OIL | 1% to 5% |
| CORN OIL | 1% to 5% |
| STEARIC ACID | 1% to 5% |
| CETYL ALCOHOL C16 C18 | 0% to 1% |
| ANTIFOAMING AGENT 70414 | 0% to 1% |
| LAURYL ALCOHOL 11OE | 1% to 5% |
| PEG 300 MONOLAURATE | 0% to 1% |
| GLYCEROL MONOLEATE | 0% to 1% |
| GLYCEROL MONOSTEARATE | 1% to 5% |
| ARABINOGALACTAN | 0% to 5% |
| PRESERVATIVES | 0% to 1% |
| CITRIC ACID MONOHYDRATE | 0% to 1% |
| TRISODIUM CITRATE | 0% to 1% |
| PURIFIED WATER | QSP 100% |
| FRAGRANCE | 0% to 1% |
| PEANUT OIL | 1% to 5% |
| HYDROGENATED PALM OIL | 1% to 5% |

| FOAM | |
|---|---|
| Raw material/brand name | % |
| PURIFIED WATER B4 | QSP 100% |
| LAUROAMPHOACETATE | 5% to 20% |
| COCOGLUCOSIDE | 5% to 20% |
| ORONAL LCG | 5% to 20% |
| HYDRIOSUL KMG 30 (2) | 5% to 20% |
| PEG 6000 DISTEARATE | 1% to 5% |
| PRESERVATIVE | 1% to 5% |
| ARABINOGALACTAN | 0% to 5% |
| CHAMOMILE EXTRACT | 1% to 5% |
| CITRIC ACID MONOHYDRATE | 0% to 1% |
| SEQUESTRANT | 0% to 1% |
| WHEAT COCOPROTEIN | 0% to 1% |
| MUSTITI 11/1 FRAGRANCE | 0% to 1% |
| SODA LYE | 0% to 1% |

| SPRAY | |
|---|---|
| Raw material/brand name | % |
| PURIFIED WATER B4 | QSP 100% |
| TRILAURETH-4 PHOSPHATE | 1% to 5% |
| DICAPRYLYL CARBONATE | 1% to 5% |
| BUTYLENE GLYCOL | 1% to 5% |
| ERYTHRITYL ESTER | 1% to 5% |
| FLUID VASELINE OIL | 1% to 5% |
| SHEA BUTTER (LIQUID) | 0% to 1% |
| PURE JOJOBA | 0% to 1% |
| PRESERVATIVES | 0% to 1% |
| ARABINOGALACTAN | 0% to 5% |
| SODA LYE | 0% to 1% |
| MUSTITI 10/3 FRAGRANCE | 0% to 1% |
| XANTHAN GUM | 0% to 1% |
| CARBOPOL 981 NF | 0% to 1% |
| SEQUESTRANT | 0% to 1% |
| CITRIC ACID MONOHYDRATE | 0% to 1% |

Example 5

Compositions to be Administered Orally

Arabinogalactan is added to oral compositions, in compounds allowing the administration of 50 to 200 mg of arabinogalactan per day.

5.1 Anti-stretch Mark Composition in Soft Capsule Form

A) Composition 1

| | |
|---|---|
| Arabinogalactan | 30 mg |
| Awara oil | 60 mg |
| Unsaponifiable-rich colza oil | 300 mg |
| Vitamin of group B (B1, B2, B3, B5, B6, B9, B12) | QSP 100% RDA |
| Tocotrienols | QSP 50% RDA |
| Vitamin E | |
| Beeswax | |
| Soya lecithin | |
| Edible gelatin | |
| Glycerin | QSP 1 soft capsule |

This composition is administered as four to six 500, mg capsules per day.

B) Composition 2

| | |
|---|---|
| Arabinogalactan | 30 mg |
| Cereal oil rich in ceramides and polar lipids | 300 mg |
| Lupin oil | 50 mg |
| Vitamin E | QSP 100% RDA |
| Vitamin C | QSP 50% RDA |
| Beeswax | |
| Soya lecithin | |
| Edible gelatin | |
| Glycerin | QSP 1 soft capsule |

This composition is administered as four to six 500, mg capsules per day.

5.2 Tablets

| | |
|---|---|
| Arabinogalactan | 25 mg |
| Cereal extracts (wheat, buckwheat, millet, spelt) rich in sulfur amino acids | 200 mg |
| Vitamin C | QSP 50% RDA |
| Fish cartilage glycosaminoglycans | 200 mg |
| Glucidex IT 19 (compression agent) | QSP 1 800 mg tablet |

This composition is administered as five to eight tablets per day.

| | |
|---|---|
| Arabinogalactan | 200 mg |
| Cereal extracts (wheat, buckwheat, millet, spelt) rich in sulfur amino acids | 200 mg |
| Zinc in chelate form | QSP 100% RDA |
| Vitamin C | QSP 50% RDA |
| Fish cartilage glycosaminoglycans | 200 mg |
| Fruit flavor (citrus, red berries), acesulfame potassium, Glucidex IT 19 (compression agent) | QSP 1 2000 mg tablet |

This composition is administered once per day.

5.3 Examples of Powder Sticks

| | |
|---|---|
| Arabinogalactan | 100 mg |
| Polyphenol-rich tea extract | 100 mg |
| OPC-rich grape extract | 50 mg |
| Plant beta glucans | 100 mg |
| Xanthan gum | 1 mg |
| Sodium ascorbate | 0.3 mg |
| Maltodextrin | QSP 5 g |

This composition is administered twice per day.

| | |
|---|---|
| Arabinogalactan | 100 mg |
| *Centella asiatica* extract | 100 mg |
| Magnesium, selenium, manganese | QSP 100% RDA |
| Xanthan gum | 1 mg |
| Sodium ascorbate | 0.3 mg |
| Maltodextrin | QSP 5 g |

This composition is administered twice per day.

5.4 Example of Chocolate-Flavored Cereal Bar

| | |
|---|---|
| Arabinogalactan | 200 mg |
| Lycopene | 6 mg |
| Astaxanthin | 4 mg |
| Fucoxanthin | 4 mg |
| Micro-encapsulated lutein | 4 mg |
| Micro-encapsulated tocotrienol | QSP 100% RDA in vitamin E |
| Dark Chocolate, oligofructose, sugar, fructose syrup, fat-reduced cocoa powder, crunchy cereals, powdered skim milk, almonds, glycerol, sorbitol, vegetable oils, glucose syrup, flavoring, sweetened condensed milk, soya lecithin, fatty acid mono- and di-glycerides, caramelized syrup, maltodextrin, salt, potassium sorbate, alpha tocopherol | QSP 1 50 g bar |

This composition is administered once per day.

5.5 Example of a Vanilla-Flavored Cereal Bar

| | |
|---|---|
| Arabinogalactan | 200 mg |
| Cereal extracts (wheat, buckwheat, millet, spelt) rich in sulfur amino acids | 200 mg |
| Fish cartilage glycosaminoglycans | 200 mg |
| Polyphenol-rich green tea extract | 200 mg |
| Oligofructose, sugar, fructose syrup, crunchy cereals, powdered skim milk, almonds, glycerol, sorbitol, vegetable oils, glucose syrup, flavoring, sweetened condensed milk, soya lecithin, fatty acid mono- and di-glycerides, caramelized syrup, maltodextrin, salt, potassium sorbate, alpha tocopherol | QSP 1 50 g bar |

This composition is administered once per day.

5.6 Example of Praline-Flavored Milk Beverage

| | |
|---|---|
| Arabinogalactan | 200 mg |
| Polyphenol-rich green tea extract | 100 mg |
| Vitamin of group B (B1, B2, B3, B5, B6, B9, B12) | QSP 100% RDA |
| Zinc, magnesium, selenium | QSP 100% RDA |
| Powdered skim milk, flavoring, fructose, egg white, hazel nuts, sugar, caramel, beta-carotene, xanthan gum, aspartame, acesulfame potassium, soya lecithin, maltodextrin | QSP 1 30 g packet |

This composition is administered once per day.

Example 6

Evaluation of an Anti-Stretch Mark Cosmetic Composition (Composition No. 2 of Example 4 Above) in a Model of Reconstructed Skin Mimicking a Stretch Mark Context and Objective of the Study The formation of stretch marks involves reorganization of the dermal extracellular matrix with an impoverishment and alteration of macromolecules (such as collagen and elastin), the component associated with an inflammatory process. Stretch marks can thus be compared to an atrophic scar.

The cicatrization process proceeds according to various stages involving both epidermal keratinocytes and dermal fibroblasts. These stages are characterized by biochemical, molecular and morphological modifications which can be identified by quantifying the expression of specific biomarkers.

The Applicant, using a total reconstructed skin model (Phenion®, Duesseldorf, Germany), has developed an experimental in vitro dermal scar model that mimics a stretch mark in order to evaluate the effectiveness of a cosmetic anti-stretch mark composition.

Methodology

Three test conditions were prepared:

Condition a: control condition of undamaged reconstructed skin (no dermal wound) not treated with the cosmetic composition.

Condition b: damaged reconstructed skin on which a dermal "wound" has been created, but on which the cosmetic composition was not applied.

Condition c: treatment with the cosmetic anti-stretch mark composition which was deposited on the surface of the reconstructed skin (topical application) just after the dermal "wound" was created.

The gene expression of the following biomarkers was measured 24 h, 48 h, 8 days and 16 days after wounding of the tissue by quantitative real-time PCR using TaqMan® technology: collagens type I and type VII, which stimulate the cicatrization process allowing rapid remodeling of the extracellular matrix; integrin beta-1, which acts on keratinocyte migration, an early stage of tissue repair; and elastin, which strengthens cutaneous tissue and which is degraded during inflammatory phenomena. The three conditions were carried out in duplicate during two independent experiments named EXP NO. 1 and EXP NO. 2.

Results and Conclusion

The data in table I below represent the relative quantities of each gene of interest (normalized by the reference gene GAPDH) expressed in condition c (skin with "wound" treated with the cosmetic anti-stretch mark composition) compared to condition b (untreated skin with "wound").

TABLE 1

Expression of genes for collagen I, collagen VII, integrin beta-1 and elastin in a model of reconstructed skin mimicking a stretch mark - Effect of the cosmetic anti-stretch mark composition.

| Condition tested | Biomarker analyzed | Experiment number | Relative quantity | | | |
|---|---|---|---|---|---|---|
| | | | 24 h | 48 h | 8 d | 16 d |
| b: dermal "wound" | All markers | EXP NO. 1 and NO. 2 | 1 | 1 | 1 | 1 |
| c: "wound" treated with the anti-stretch mark composition | Collagen I | EXP NO. 2 | 0.84 | 1.26 | 1.70 | 0.75 |
| | Collagen VII | EXP NO. 1 | 1.13 | 0.96 | 3.08 | 4.94 |
| | Integrin beta-1 | EXP NO. 1 | 1.26 | 0.83 | 1.72 | 2.31 |
| | | EXP NO. 2 | 0.72 | 2.04 | 2.29 | 3.13 |
| | Elastin | EXP NO. 1 | 1.61 | 0.42 | 2.24 | 0.66 |
| | | EXP NO. 2 | 1.86 | 2.09 | 5.2 | 0.66 |

In this skin model mimicking a stretch mark (with dermal "wound"), the topical application of the cosmetic anti-stretch mark composition is able to, after 8, days, increase the expression of collagens I and VII, integrin beta-1 and elastin (by factors of 1.7, 3.08, 2.29 and 5.2, respectively). This effect is amplified up to the 16th day for collagen VII and integrin beta-1 (factors of 4.9 and 3, respectively).

Thus the cosmetic anti-stretch mark composition tested shows, in this model mimicking a stretch mark, a dual mechanism of action based on:
- tissue regeneration, by stimulating intercellular communications at the dermis-epidermis junction, enabling early reorganization of cutaneous tissue and countering matrix degradation (integrin beta-1 and collagen VII);
- remodeling of the dermal matrix, by reestablishing a certain resistance and strength to the dermal extracellular matrix (collagen I and elastin).

Example 7

Evaluation of the Effect of a Topical Treatment of Recent Stretch Marks Among Women After Childbirth The Applicant studied the response of recent, clinically active stretch marks to topical application of a cream formulated in a specific way to reduce stretch marks.

The cream corresponds to composition no. 2 of example 4 above.

Protocol
Study Design

In a comparative, single-blind, randomized, intra-individual study of 22 postpartum women with recent, symmetrical and comparable stretch marks (stage I in the Deprez-Adatto classification: see table 2 below) on each of their thighs or hips at the baseline, the cream was applied in gentle circular massages twice a day to one of their thighs for three months. The other thigh served as untreated control. Each thigh was evaluated monthly by clinical examinations and by measurements using instruments. The women also applied the cream to all regions concerned by stretch marks in order to obtain an overall evaluation of effectiveness.

The women who participated in the study had a normal body mass index (BMI between 19 kg/m$^2$ and 25 kg/m$^2$) and were between 18 and 40 years of age.

The significance level was set at 5% (Student's t-test and Wilcoxon test).

TABLE 2

Classification of stretch marks (Deprez-Adatto; see Adatto M. A., Deprez P., Journal of Cosmetic Dermatology, 2(2): 61-67, April 2003.)

| Clinical classification of stretch marks | Clinical appearance |
|---|---|
| Stage I | Stretch marks that are recent, inflammatory, usually purplish. |
| Stage II a | Stretch marks that are white, superficial, without transverse lines (ladder rungs) and without palpable depression on the surface of the skin. |
| Stage II b | Stretch marks that are white, superficial, without transverse lines (ladder rungs) but with palpable depression on the surface of the skin. |
| Stage III a | Stretch marks that are white, with atrophic base, with transverse lines (ladder rungs) measuring less than 1 cm in width, without a pearl-white base. |
| Stage III b | Stretch marks that are white, with atrophic base, with transverse lines (ladder rungs) measuring less than 1 cm in width, with a pearl-white base. |
| Stage IV | Stretch marks that are white, with atrophic base, with transverse lines (ladder rungs) measuring greater than 1 cm in width, with a pearl-white base. |

Evaluation Criteria

The evaluation criteria are presented in table 3 below.

TABLE 3

| Evaluation | Analysis | D0 | D28 | D56 | D84 |
|---|---|---|---|---|---|
| Clinical evaluation using predefined scales | Treated/ untreated | X | X | X | X |
| Centimeter measurements of stretch marks | Treated/ untreated | X | X | X | X |
| Measurement of moisturizing degree using a Corneometer ® | Before/ after | X | X | X | X |
| Subjective evaluation by questionnaire | Before/ after | X | X | X | X |
| Parallel-light macro photography | Before/ after | X | | | X |

TABLE 3-continued

| Evaluation | Analysis | D0 | D28 | D56 | D84 |
|---|---|---|---|---|---|
| Cross-polarization photography (Nikon D70): evaluation of the erythematous component | Before/after | X | | | X |
| Overall tolerance score | Before/after | X | | | X |
| Recording of adverse events | Before/after | X | X | X | X |

Results:

Effectiveness of the Cream on Recent Postpartum Stretch Marks

Figure 6:
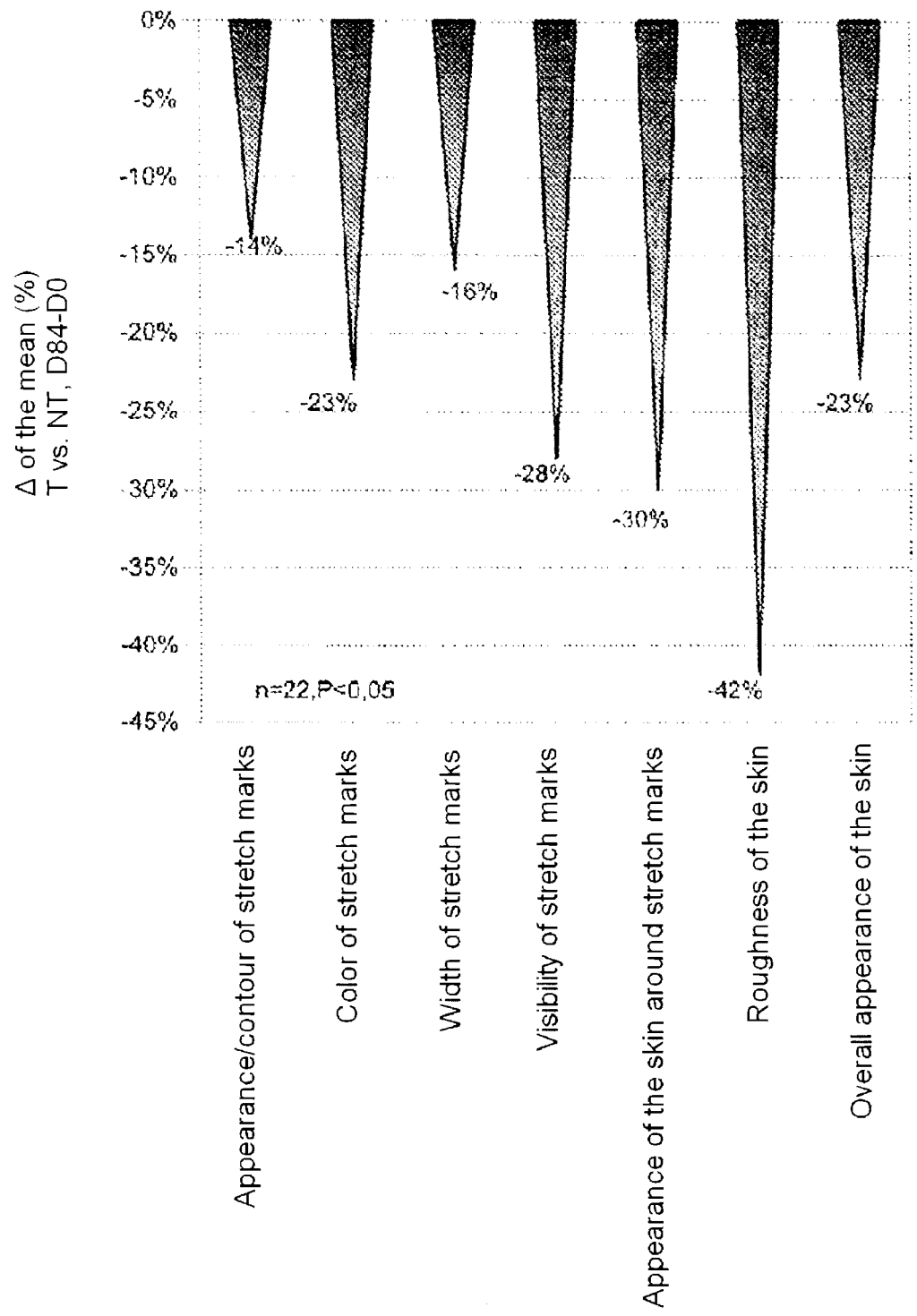
FIG. 6: Clinical evaluation of the progression of parameters of color, appearance, width, etc., of stretch marks after three months of treatment

FIG. 6 corresponds to the clinical evaluation of the progression of the parameters of color, appearance, width, etc., of stretch marks after three months of treatment.

After applying the composition for a period of three months, it was observed that all the parameters evaluated (appearance/contour of stretch marks, color of stretch marks, width of stretch marks, visibility of stretch marks, appearance of the skin around stretch marks, roughness of the skin around stretch marks, overall appearance of the skin) are statistically improved. Moreover, the skin seemed firmer (+31%) and appeared more moisturized (+50%).

Overall, the clinician observed a significant overall improvement for 100% of the subjects: 31% had great improvement and 69% had average improvement.

Figure 7:
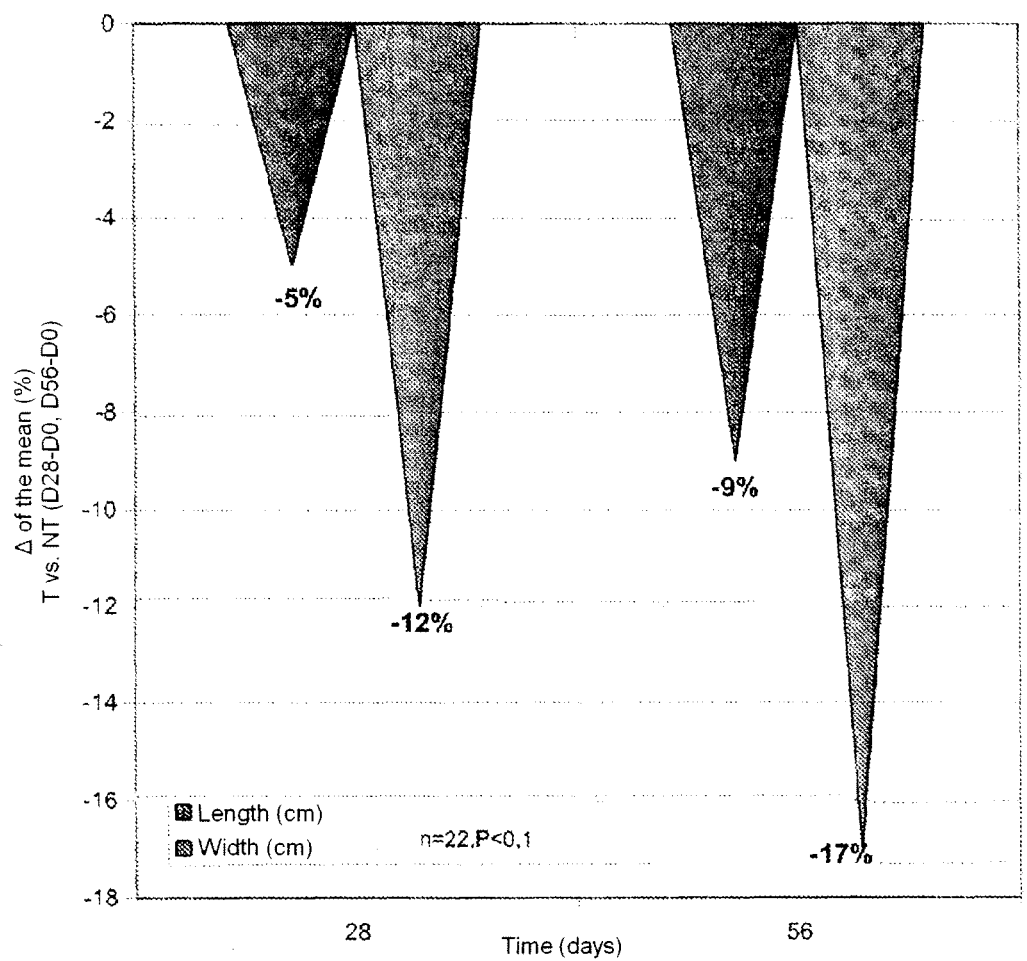
FIG. 7: Progression of stretch marks in centimeter measurements

FIG. 7 corresponds to the progression of stretch marks using centimeter measurements. In this figure, a significant reduction in the dimensions (length and width) of treated stretch marks is observed.

Figure 8:
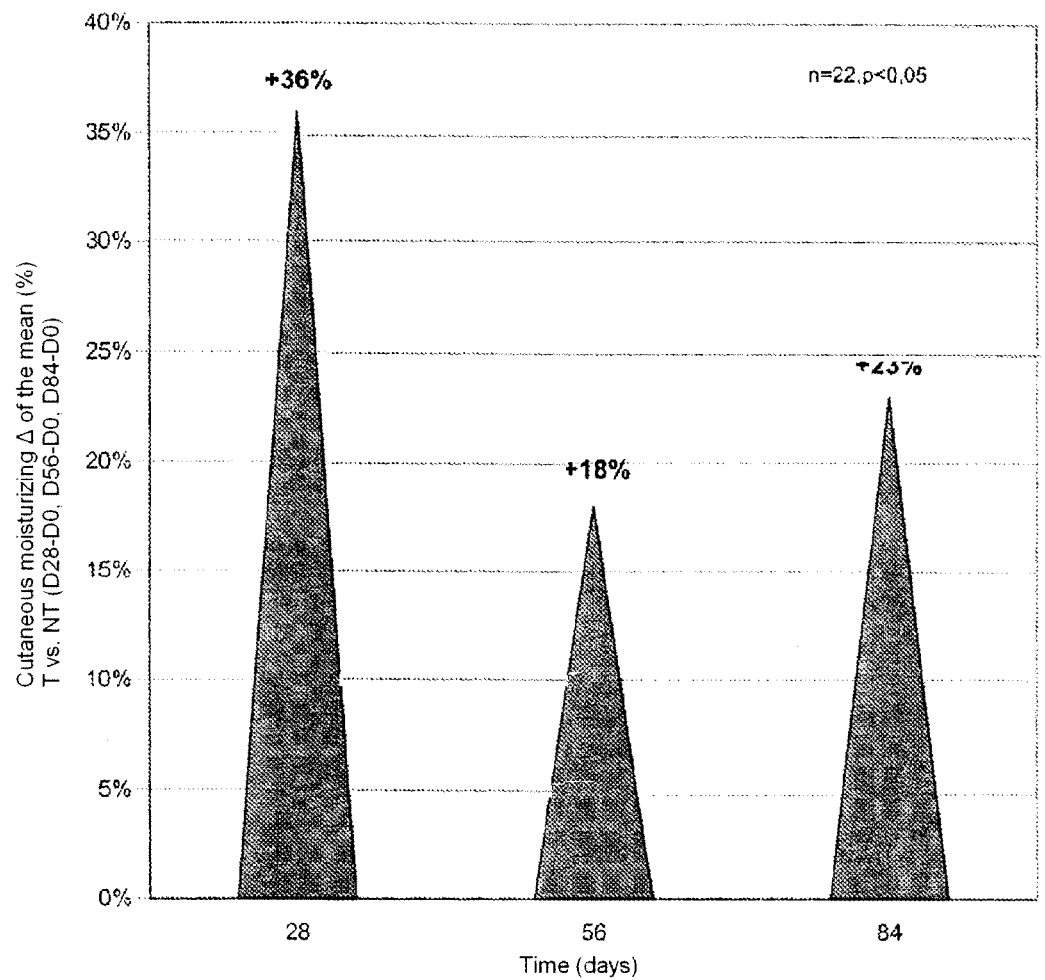
FIG. 8: Evaluation of moisturizing degree measurements

FIG. 8 corresponds to the evaluation of the measurement of moisturizing degree. In this figure, measurements showed a significant improvement (+23%) of the level of moisturizing of the skin after a three-month test.

Figure 9:
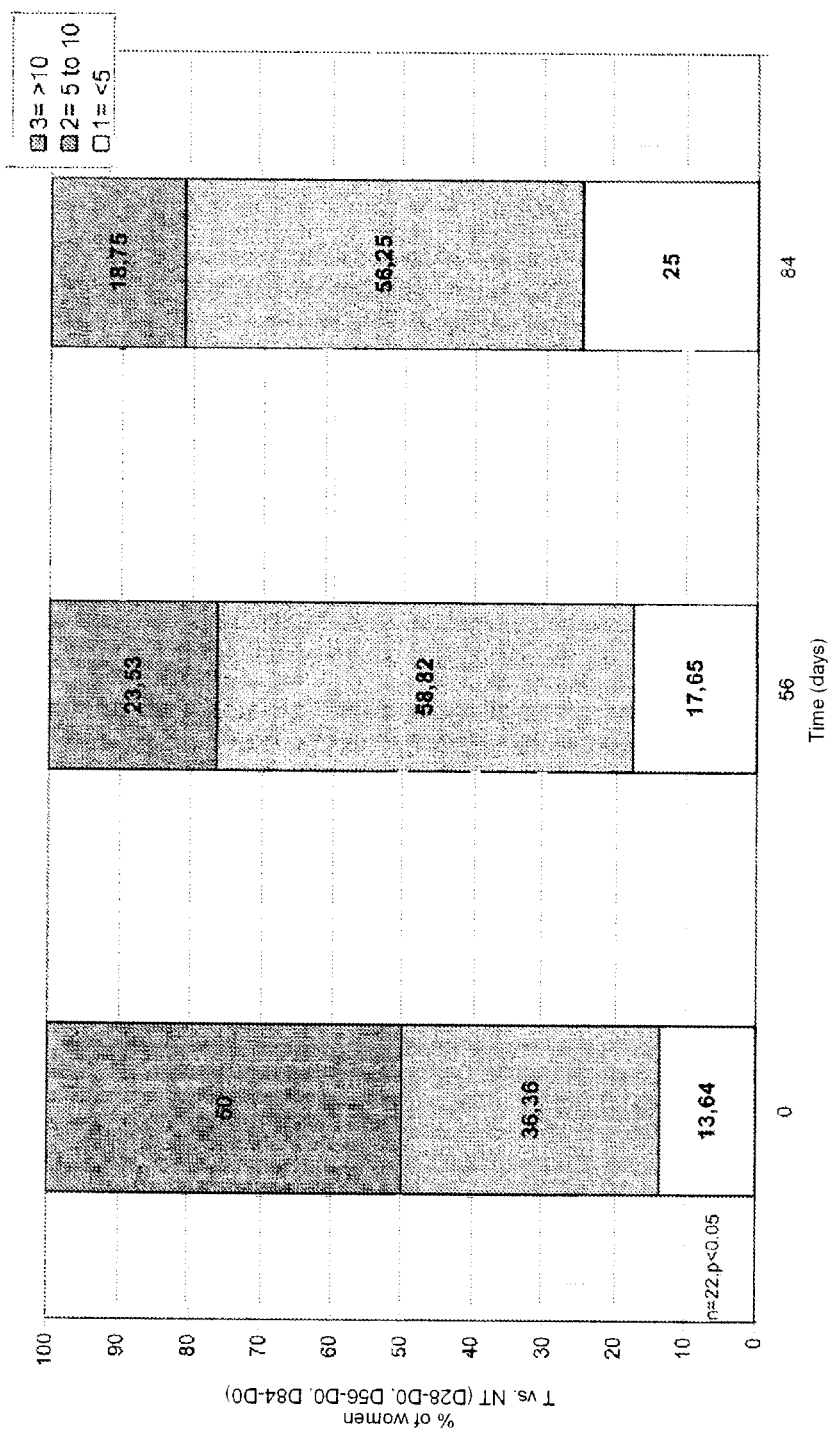
FIG. 9: Progression of number of stretch marks
Figure 10:
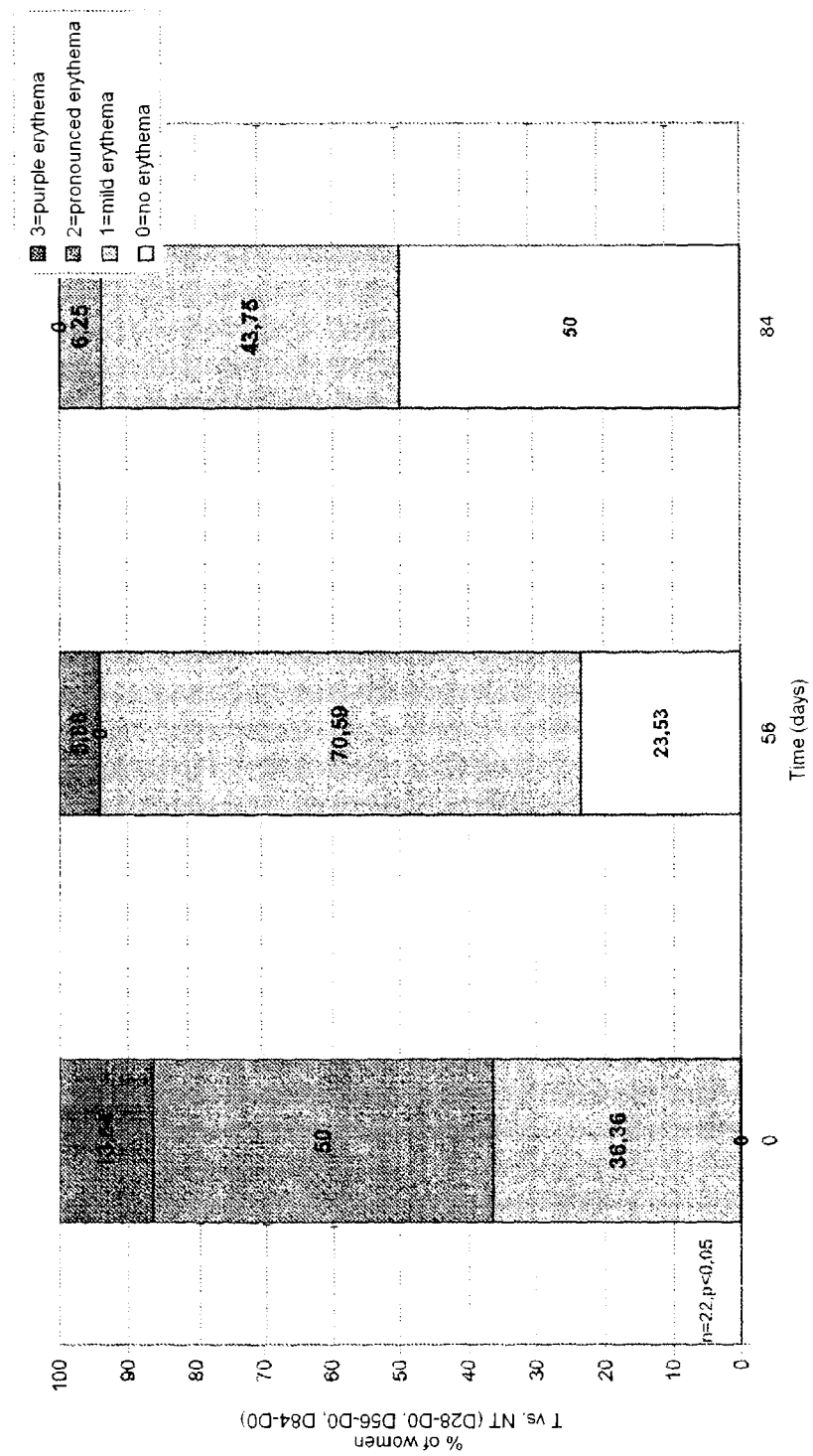
FIG. 10: Progression of total erythema
Figure 11:
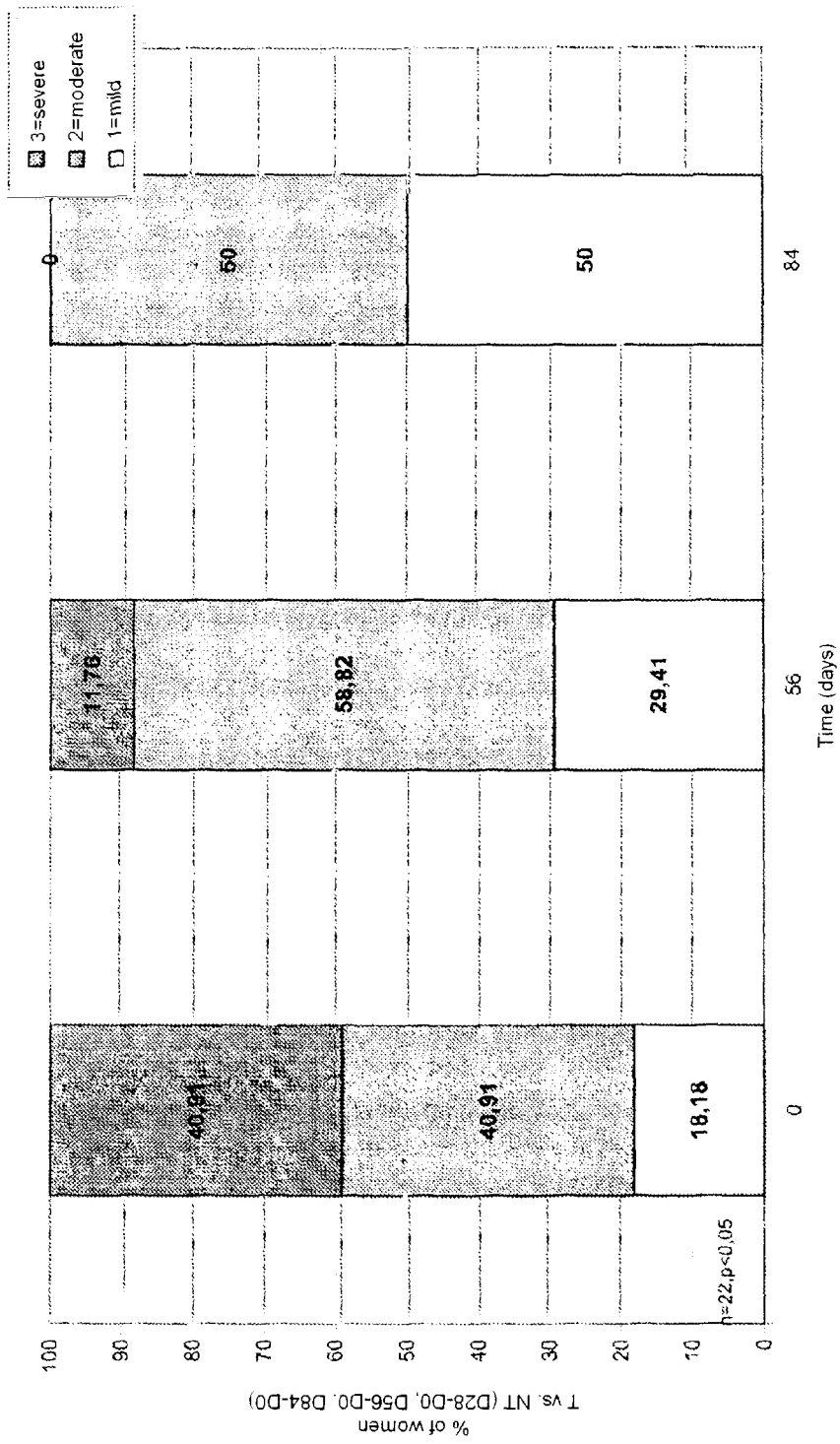
FIG. 11: Progression of the severity index

FIGS. 9, 10 and 11 correspond to the progression of the severity of the stretch marks. More precisely, FIG. 9 shows the progression of the number of stretch marks, FIG. 10 shows the progression of the overall erythema, and FIG. 11 shows the progression of the severity index.

After 3 months, the clinician observed a genuine improvement in stretch marks: a significant reduction in erythema (observed in 75% of the women) and in the severity index (observed in 87% of the women).

Table 4 below presents the self-evaluation results and indicates the percentage of agreement (complete agreement and agreement).

TABLE 4

| Effectiveness on stretch marks | After 3 months |
|---|---|
| Reduction in the contour of the stretch marks | 81% |
| Improvement in the appearance of the skin around the stretch marks | 81% |
| Improvement in the color of the stretch marks | 100% |
| Improvement in the overall appearance of the stretch marks | 88% |
| Improvement in the overall appearance of the skin | 88% |
| The skin is more supple | 81% |
| The skin is smoother | 75% |
| The skin is softer | 88% |
| The stretch marks are less visible | 75% |
| The product is effective on stretch marks | 94% |

The answers given to the subjective evaluation questionnaire clearly confirmed the preceding results. The product was rated positively for its effectiveness on stretch marks and skin quality and also for its organoleptic properties.

Overall satisfaction rate: 88% of the volunteers would like to continue using the cream.

The product has very good cutaneous tolerance. Not one adverse event was reported during the study.

CONCLUSION

This anti-stretch mark composition, containing arabinogalactan as well as lupeol and natural biopeptides, has a statistically significant effect on active recent stretch marks among postpartum women. Moreover, an improvement after 28 days, which continues up to three months, is observed.

The composition thus provides:
  A clear improvement in the overall quality of the skin as well as stretch marks.
  A significant overall improvement in the severity of stretch marks.
  A significant reduction in the dimensions (width and length) of treated stretch marks.
  A visible reduction in overall erythema.
  Good tolerance and safety profiles.

The invention claimed is:

1. A method of cosmetic prevention and/or treatment of striae distensae (stretch marks) on the skin, comprising administering a composition containing an effective amount of arabinogalactan as an active principle to a person that may develop or has stretch marks.

2. The method according to claim 1, wherein the composition is administered topically.

3. The method according to claim 1, wherein the composition is administered orally.

4. The method according to claim 1, wherein the arabinogalactan is extracted from larch (genus *Larix*).

5. The method according to claim 1, wherein the arabinogalactan is present in said composition in a proportion between 0.01% and 10% by weight compared to the total weight of the composition.

6. The method according to claim 1, wherein said composition contains at least one other anti-stretch mark agent selected from the group consisting of: lupeol, soya peptides, tripeptides composed of the amino acids glycine, histidine and lysine, sophora flower extract, chlorphyceae extract, peptide extract of avocado, panthenol, and mixtures thereof.

7. The method according to claim 1, wherein said composition is intended to prevent the appearance of stretch marks during pregnancy.

8. A cosmetic method for the prevention and/or the treatment of the appearance of stretch marks on the skin comprising administrating to a patient in need thereof a cosmetic composition comprising an effective amount of arabinogalactan as an active principle.

9. A method for the prevention and/or treatment of the appearance of stretch marks on the skin, comprising administrating to a patient in need thereof a dermatological composition comprising an effective amount of arabinogalactan as an active principle.

10. A method for the prevention and/or treatment of the appearance of stretch marks on the skin, comprising administrating to a pregnant patient a dermatological composition comprising an effective amount of arabinogalactan as an active principle during pregnancy.

11. A cosmetic method for the prevention and/or the treatment of the appearance of stretch marks on the skin comprising administrating to a pregnant patient a cosmetic composition comprising an effective amount of arabinogalactan as an active principle during pregnancy.

* * * * *